United States Patent
Constantin et al.

(10) Patent No.: US 10,026,517 B2
(45) Date of Patent: Jul. 17, 2018

(54) MULTILEAF COLLIMATOR ASSEMBLY WITH REDUCED EXTRA-FOCAL LEAKAGE

(71) Applicant: Varian Medical Systems, Inc., Palo Alto, CA (US)

(72) Inventors: Magdalena Constantin, Los Altos, CA (US); HsinLu Hsu, Sunnyvale, CA (US); Jonathan Evans, Mountain View, CA (US); Robert Kopels, Cupertino, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 241 days.

(21) Appl. No.: 14/859,048

(22) Filed: Sep. 18, 2015

(65) Prior Publication Data

US 2017/0084359 A1    Mar. 23, 2017

(51) Int. Cl.
*G21K 1/04* (2006.01)
*A61N 5/10* (2006.01)

(52) U.S. Cl.
CPC .......... *G21K 1/046* (2013.01); *A61N 5/1045* (2013.01)

(58) Field of Classification Search
CPC ...... A61N 5/1042; A61N 5/1045; G21K 1/04; G21K 1/046
See application file for complete search history.

(56) References Cited

U.S. PATENT DOCUMENTS

| | | | | |
|---|---|---|---|---|
| 4,794,629 A * | 12/1988 | Pastyr | ............... | A61N 5/1042 378/146 |
| 5,012,506 A * | 4/1991 | Span | ............... | G21K 1/04 250/505.1 |
| 5,144,647 A * | 9/1992 | Kikuchi | ............... | G21K 1/04 250/505.1 |
| 8,637,841 B2 * | 1/2014 | Prince | ............... | A61N 5/1045 250/492.1 |
| 9,082,520 B2 * | 7/2015 | Prince | ............... | A61N 5/1045 |
| 2004/0082855 A1 * | 4/2004 | Robar | ............... | A61N 5/10 600/436 |
| 2004/0184578 A1 * | 9/2004 | Nakano | ............... | A61N 5/103 378/65 |
| 2008/0177179 A1 * | 7/2008 | Stubbs | ............... | A61N 5/1049 600/431 |
| 2011/0033028 A1 * | 2/2011 | Parsai | ............... | A61N 5/1042 378/65 |
| 2012/0043482 A1 * | 2/2012 | Prince | ............... | A61N 5/1045 250/505.1 |
| 2014/0112453 A1 * | 4/2014 | Prince | ............... | A61N 5/1045 378/152 |
| 2017/0084359 A1 * | 3/2017 | Constantin | ............ | G21K 1/046 |

* cited by examiner

*Primary Examiner* — Thomas R Artman
(74) *Attorney, Agent, or Firm* — Houst Consulting (57) ABSTRACT

A multileaf collimator assembly employs one or more static blocks to significantly reduce extra focal leakage or out of field dose. The multileaf collimator assembly includes a plurality of pairs of beam shaping leaves. The leaves of each pair are movable relative to each other in a longitudinal direction. The one or more static blocks are disposed adjacent to the outermost pair of beam shaping leaves and unmovable in the longitudinal direction. The material composition and geometric characteristics of the static blocks may be chosen based on the pre-determined leakage specification for a particular radiation apparatus in the patient plane.

30 Claims, 8 Drawing Sheets

MULTILEAF COLLIMATOR ASSEMBLY WITH REDUCED EXTRA-FOCAL LEAKAGE

TECHNICAL FIELD

Embodiments of this disclosure relate generally to radiation apparatuses and methods. In particular, various embodiments of a multileaf collimator assembly capable of significantly reducing extra-focal radiation leakage in the proximity of intended radiation treatment area are described.

BACKGROUND

Multileaf collimators (MLCs) are widely used in radiation machines to support various radiation treatments. A multileaf collimator includes a plurality of beam shaping leaves independently movable in and out of a radiation beam to block or modify the beam. The beam shaping leaves are generally arranged in pairs and disposed in opposing banks. The combined positioning of all leaves may define one or more apertures through which an unblocked radiation beam passes. The one or more apertures may define a treatment field in the isocenter plane, with a size and/or shape generally conforming to the size and/or shape of a target located in the isocenter plane. A maximal treatment field is generally provided when all the beam shaping leaves are fully retracted.

Figure 1:
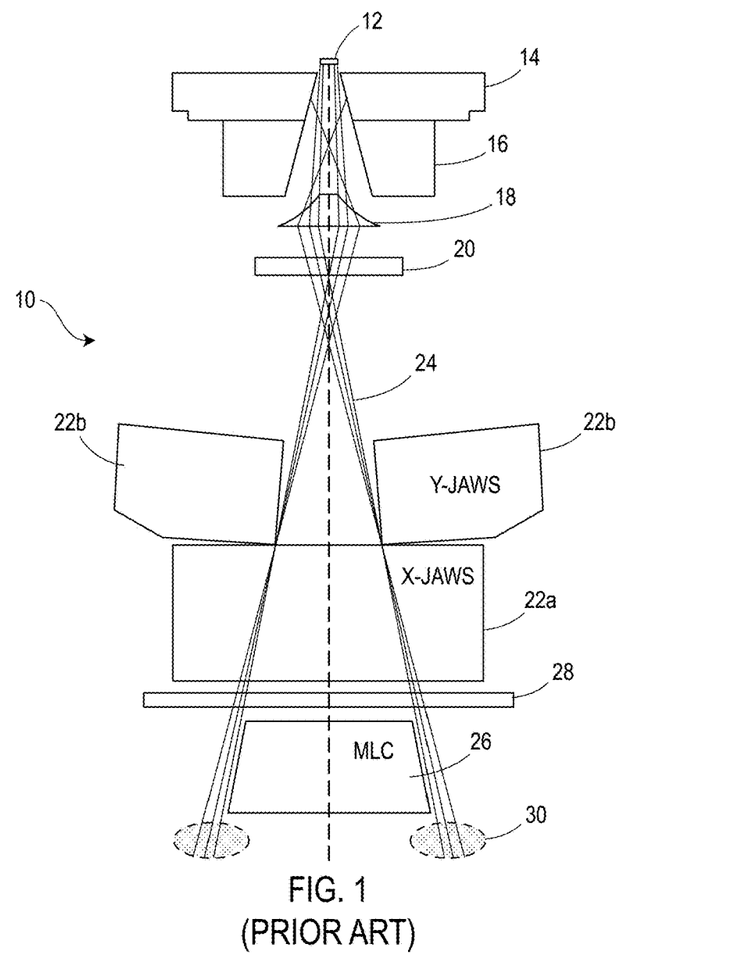
FIG. 1 depicts a conventional radiation apparatus.

FIG. 1 depicts a conventional radiation machine 10 including an MLC in conjunction with collimation jaws. The radiation machine 10 includes a radiation source 12, a primary collimator 14 and a secondary collimator 16 adjacent to the source 12, flattening filters 18, and an ion chamber 20. The radiation machine 10 also includes collimation jaws 22a and 22b that can be motorized and positioned to generally limit the size of the beam 24 from the source 12. An MLC 26, supported by a mounting plate or MLC interface plate 28, further collimates the beam in finer resolutions to provide a treatment field with a size and/or shape generally conforming to an intended target in the isocenter plane.

Figure 1A:
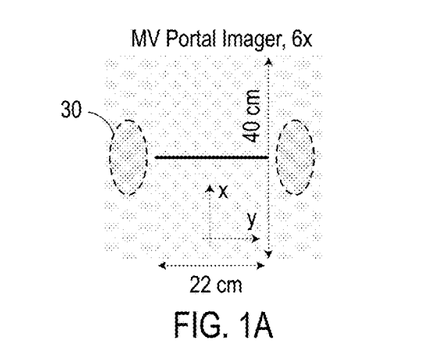
FIG. 1A is a graph showing extra-focal leakage measurement with an MLC being closed on axis using the portal imager at 6 M.

In the conventional radiation machine 10 shown in FIG. 1, a significant extra-focal dose 30 may appear in the proximity of an intended treatment field, especially when the intended treatment field comes near the edge of the maximal treatment field of the MLC 26 as the collimation jaws 22a and 22b are forced to open to a large field. The extra-focal leakage is caused in part by the radiation scatter through the gap between the collimation jaws e.g. Y-jaws 22b and the outermost beam shaping leaves of the MLC 26. As the size of an intended treatment field increases, the extra-focal dose or out-of-field dose (OOFD) 30 delivered to the patient also increases. A few scattered photon trajectories are schematically shown to originate from the flattening filter 18 which is the main source of scattered radiation. Additionally, scatter from the upper collimator 14, ion chamber 20, jaws and MLC leaves 26 also contribute to the extra-focal dose. FIG. 1A schematically shows an extra-focal leakage measurement outside a field with the MLC being closed on axis.

Extra-focal leakage may lead to considerable dose to surrounding critical organs and/or healthy tissue, creating higher secondary cancer risk. Therefore, it is desirable to develop a multileaf collimator assembly capable of preventing or significantly reducing extra-focal radiation leakage in the proximity of the outermost MLC leaves.

SUMMARY

Certain embodiments of a multileaf collimator assembly and a radiation apparatus are set forth below. It should be understood that these embodiments are presented merely to provide the reader with a brief summary of certain forms the invention might take and that these embodiments are not intended to limit the scope of the invention. Indeed, the invention may encompass a variety of embodiments or aspects that may not be set forth below.

In one aspect, a multileaf collimator assembly that can significantly reduce extra-focal leakage or out-of-field dose ("OOFD") is provided. The multileaf collimator assembly is designed and optimized to ensure as low as reasonably achievable radiation (ALARA) for the patient outside the intended treatment field. In a specific embodiment, the multileaf collimator assembly includes two outboard blocks mounted on the MLC interface plate, between the fixed leaf boxes of multileaf collimator (MLC). The outboard blocks can be static or non-motorized. The outboard blocks serve to block the leakage path for the upper collimator scatter (e.g. extra-focal scatter) that reaches the patient plane in the area outside the intended treatment field. In conventional radiation machines, leakage paths exist due to the physical gaps between the movable collimation jaws and the outermost MLC leaves, creating unintended radiation hot spots outside the treatment area. The outboard blocks can be designed to be cost-effective in weight and easily dismounted for MLC service. Mounting means such as two through holes can be provided in the blocks to allow them to be mounted with long screws. The long screws increase the ability of the joint to resist loosening of the fasteners. It also simplifies the rough shape of the blocks and reduces the cost of the part. The outboard blocks can also be designed to not require precision tolerances for the mounting features or for the outside dimensions. This may further reduce costs without significantly sacrificing performance.

In another aspect, a radiation apparatus including an MLC assembly that can significantly reduce extra-focal dose outside an intended treatment field, independent of its size or shape, is provided. In a specific embodiment, the radiation apparatus is free of a flattening filter. In another specific embodiment, the radiation apparatus is free of movable collimation jaws. In a further specific embodiment, the radiation apparatus is free of a flattening filter and movable collimation jaws. The radiation apparatus may include two outboard blocks to block extra-focal leakage. The outboard blocks may be static or non-motorized and located adjacent to the outermost MLC leaves. In a specific embodiment, the MLC leaves may be arranged in two levels, one proximal to the radiation source and another distal to the radiation source. The two level MLCs may be mounted in two opposing, two-level leaf boxes which may be static. The outboard blocks may be located at the level proximal to the radiation source and mounted to the MLC interface plate to facilitate serviceability and reduce costs. Alternatively, the outboard blocks may be located at the level distal to the radiation source and secured to the MLC box. In some embodiments, a combination of proximal outboard blocks mounted on the MLC plate and distal outboard blocks secured to the leaf box may be used. The outboard blocks can be in various shapes and/or sizes and can be designed or optimized using Monte Carlo simulation methods. The typical materials for the outboard blocks include tungsten, lead, or steel alloys depending on the geometrical constraints of the lower treatment head.

Other aspects and embodiments of the disclosure are described further in the section of Detailed Description.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION

Various embodiments of a multileaf collimator assembly and a radiation machine are described. It is to be understood that the disclosure is not limited to the particular embodiments described as such may, of course, vary. An aspect described in conjunction with a particular embodiment is not necessarily limited to that embodiment and can be practiced in any other embodiments.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. In the following description, well known components or steps may not be described in detail in order to avoid unnecessarily obscuring the embodiments of the disclosure.

As used herein, the term "multileaf collimator" or "MLC" refers to a device that includes a plurality of beam shaping leaves each of which can be independently moved in and out of a beam to modify one or more parameters of the beam such as the beam shape, size, energy, or intensity etc. The beam shaping leaves are generally arranged in pairs and disposed in opposing banks. The beam shaping leaves of each pair may be longitudinally movable relative to each other. The longitudinal movement of individual MLC leaves may be actuated by individual drive motors. In some embodiments, the beam shaping leaves may be carried by a carriage or supported by a box structure. The carriage may be translated or the box structure may be rotated by a separate driving mechanism. Therefore, in addition to the longitudinal movement of individual MLC leaves, the carriage or box structure may further translate and/or rotate the MLC leaves collectively. In some embodiments, the beam shaping leaves may be arranged in two or more levels, e.g. an upper level proximal to the radiation source and a lower level distal to the radiation source.

As used herein, the term "maximal treatment field" refers to a treatment field in the isocenter plane when all the beam shaping leaves of a multileaf collimator are fully retracted. In general, the maximal treatment field of an MLC is in the shape of a square or rectangle. As used herein, the term "MLC center line" refers to a line perpendicular to the longitudinal moving direction of the MLC leaves and across the middle of the square or rectangle of the maximal treatment field.

The term "intended treatment field" refers to a treatment field in the isocenter plane that has a size and/or shape corresponding to the size and/or shape of an intended target in the isocenter plane. The size and/or shape of an intended treatment field can be defined by coordinately positioning the beam shaping leaves of an MLC in proper locations relative to the radiation beam.

The term "static block," which may be used interchangeably with the term "outboard block" in this disclosure, refers to a block disposed adjacent to an outermost beam shaping leaf of an MLC to reduce extra-focal leakage. In comparison with the individual MLC beam shaping leaves, a static block is not individually motorized, or does not longitudinally move in and out of the beam as individual MLC leaves do. In embodiments where MLC leaves may be collectively translated or rotated, a static block may be translated or rotated with the MLC leaves collectively as a whole. In some embodiments, the MLC may be designed to include extra MLC pairs to serve the function of the static blocks. The extra MLC pairs may be motorized blocks and have the same or greater thickness.

As used herein, the term "collimation jaws" refer to one or two pairs of beam attenuating blocks each of which can be moved in a direction generally traversing the elongate axis of the beam attenuating blocks, analogous to the opening and closing of jaws. Collimation jaws are typically motorized and positioned to generally define the size of a beam when MLC leaves are fully retracted or absent.

As used herein, the term "extra-focal" radiation or "out of field dose" ("OOFD") refers to secondary scatter radiation originating from collimation parts such as primary and secondary collimators adjacent to a radiation source or additional beam shaping elements such as flattening filters, scatter plates, jaws or MLC leaves. Extra-focal dose to the critical organs and healthy tissue in the proximity of an intended target is undesirable and should be minimized or reduced as low as reasonably achievable.

A multileaf collimator assembly is provided. The multileaf collimator assembly comprises a plurality of pairs of beam shaping leaves. The leaves of each pair are movable relative to each other in a longitudinal direction. The plurality of pairs of beam shaping leaves include a first outermost pair of leaves and a second outermost pair of leaves opposite to the first outermost pair of leaves. The multileaf collimator further comprises a first static block adjacent to the first outermost pair of leaves. The first static block is unmovable in the longitudinal direction relative to the plurality of pairs of beam shaping leaves. In some embodiment, the multileaf collimator assembly further comprises a second static block adjacent to the second outermost pair of leaves, and the second static block is unmovable in the longitudinal direction relative to the plurality of pairs of beam shaping leaves.

The plurality of pairs of beam shaping leaves may be supported by one or more box structures. The one or more box structures may be mounted to an interface plate member. The first and second static blocks may also be mounted to the interface plate member via mounting means such as through holes provided in the static blocks and long screws. Alternatively, the first and second static blocks may be mounted to the one or more box structures via suitable mounting means.

In some embodiments, the plurality of pairs of beam shaping leaves may be arranged at a first level proximal to the radiation source and a second level distal to the radiation source, and the first and second static blocks may be located at the first level adjacent to the outermost pairs of beam shaping leaves. Alternatively, the first and second static blocks may be located at the second level adjacent to the outermost pairs of beam shaping leaves.

The first and second static blocks may be disposed generally symmetrically on the center line of the multileaf collimator assembly.

A radiation apparatus is provided. The radiation apparatus comprises a radiation source and a multileaf collimator assembly. The multileaf collimator assembly comprises a plurality of pairs of beam shaping leaves. The leaves of each pair are movable relative to each other in a longitudinal direction. The plurality of pairs of beam shaping leaves include a first outermost pair of leaves and a second outermost pair of leaves opposite to the first outermost pair of leaves. The multileaf collimator further comprises a first static block adjacent to the first outermost pair of leaves. The first static block is unmovable in the longitudinal direction relative to the plurality of pairs of beam shaping leaves. In some embodiments, the multileaf collimator assembly further comprises a second static block adjacent to the second outermost pair of leaves, and the second static block is unmovable in the longitudinal direction relative to the plurality of pairs of beam shaping leaves.

The radiation apparatus may be free of a flattening filter. The radiation apparatus may also be free of a motorized collimation jaw.

Embodiments of a multileaf collimator assembly and a radiation machine will now be described with reference to the figures. It should be noted that some figures are not necessarily drawn to scale. The figures are only intended to facilitate the description of specific embodiments, and are not intended as an exhaustive description or as a limitation on the scope of the disclosure.

Figure 2:
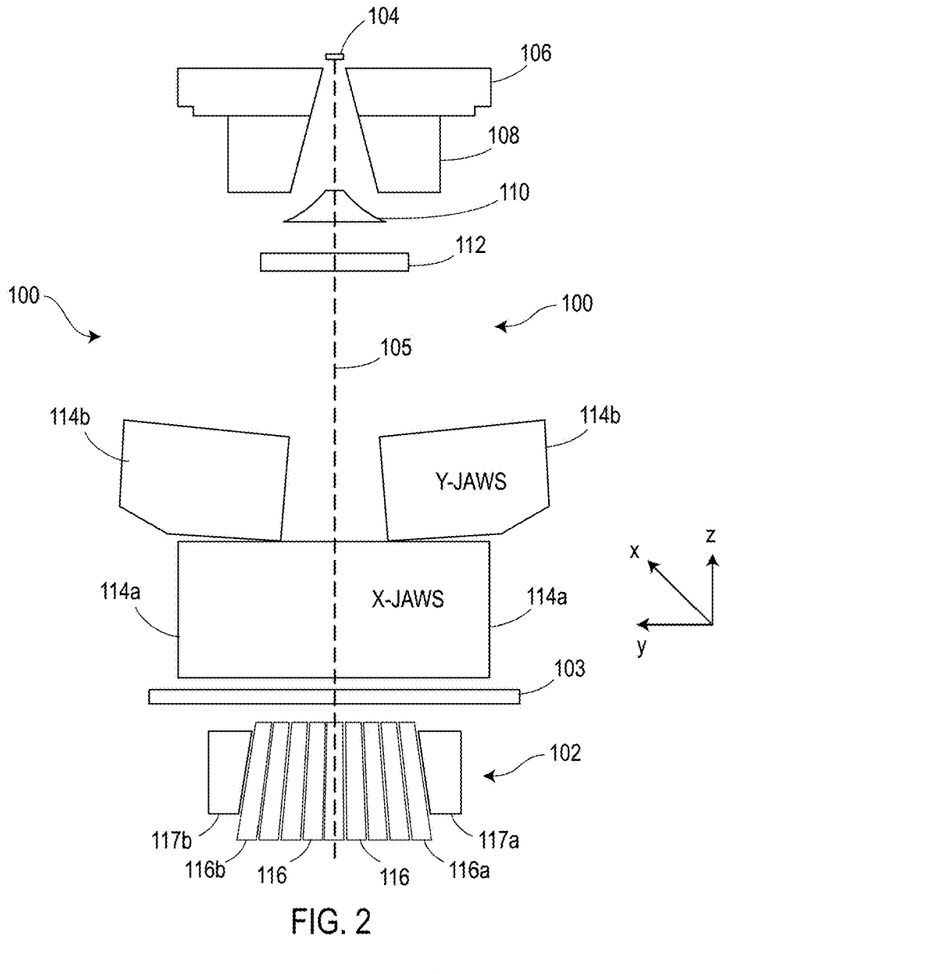
FIG. 2 depicts a radiation apparatus including an MLC assembly comprising outboard blocks according to some embodiments of this disclosure.

FIG. 2 is a simplified illustration of a radiation apparatus 100 that includes an MLC assembly 102 according to some embodiments of the disclosure. The radiation apparatus 100 includes a radiation source 104 configured to produce radiation beams such as of photons or other types of radiation. For example, the radiation source 104 may include a target which can produce x-ray radiation when impinged by energetic electron beams. The radiation apparatus 100 may include beam shaping components such as a primary collimator 106 and a secondary collimator 108 to generally limit the extent of the beam as it travels away from the radiation source 104 toward an isocenter plane. The radiation apparatus 100 may also include a flattening filter 110 configured to provide a uniform dose distribution and an ion chamber 112 to monitor the parameters of the beam.

The radiation apparatus 100 may include one or two pairs of collimation jaws, for example, lower X-jaws 114a and/or upper Y-jaws 114b. The lower X-jaws 114a may be motorized to move in the X-direction generally parallel with the MLC leaf longitudinal moving direction. The upper Y-jaws 114b may be motorized to move in the Y-direction generally traversing the MLC leaf longitudinal moving direction. The movable lower X-jaws 114a and/or upper Y-jaws 114b can provide for any rectangular shaping and sizing of the beam with an upper threshold defined by the maximum field size. In some embodiments, the radiation apparatus 100 may include only one pair of the collimation jaws in conjunction with the MLC assembly 102 of this disclosure. In some embodiments, the radiation apparatus 100 does not require any collimation jaws; the inclusion of the MLC assembly 102 of this disclosure may effectively replace both the upper and lower collimation jaws, as will be described in conjunction with other embodiments of this disclosure.

The MLC assembly 102 may be supported by a mounting plate or an MLC interface plate 103, which may be actuated, e.g. to rotate the MLC assembly 102 about the beam centerline 105. The MLC assembly 102 may include a plurality of beam shaping leaves 116 each of which is longitudinally movable, or movable along the elongate axis of the beam shaping leaves (X-direction in FIG. 2). For example, each of the beam shaping leaves 116 can be independently moved in and out of a beam. The plurality of beam shaping leaves 116 are generally arranged in pairs and disposed in opposing banks. For clarity only one of the two banks of the MLC assembly 102 is shown in FIG. 2 and the opposing bank is not shown. Each of the individual beam shaping leaves 116 may be driven by an individual drive motor (not shown). In some embodiments, the plurality of beam shaping leaves 116 may be carried by one or more carriages or supported by one or more box structures (not shown). The carriages or box structures may be further translated or rotated by a separate driving mechanism. Therefore, in addition to the longitudinal movement of individual MLC leaves 116, the MLC assembly 102 as a whole may be further rotated and/or translated.

The MLC assembly 102 may further include one or more static blocks 117 configured to reduce extra-focal leakage. For example, in some embodiments, a static block 117a may be disposed adjacent to an outermost leaf 116a, or a static block 117b may be disposed adjacent to an outermost leaf 116b. In some embodiments, two static blocks may be disposed adjacent to two opposing outmost leaves respectively. For example, a first static block 117a and a second static block 117b may be disposed adjacent to a first outermost leaf 116a and a second outermost leaf 116b respectively. As opposed to the individual beam shaping leaves 116, the static blocks 117 do not individually move in and out the beam in the longitudinal direction (X-direction). The static blocks 117 do not need to be driven by individual driving motors.

The static block(s) 117 may be mounted to the MLC interface plate 103. In some embodiments, the static block(s) 117 may be mounted to the one or more box structures which support the plurality of beam shaping leaves 116. The static block(s) 117 may be disposed generally symmetrically on the centerline of the MLC assembly 102.

Figure 2A:
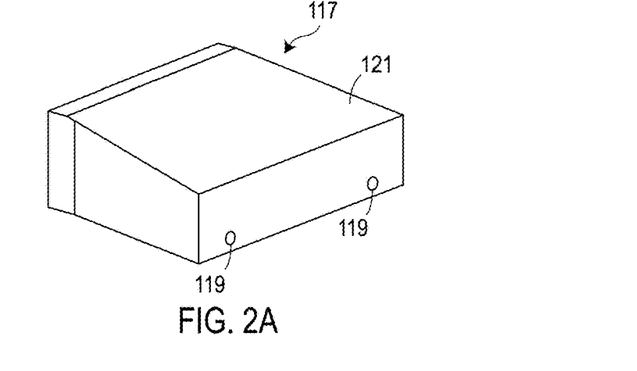
FIG. 2A depicts an exemplary outboard block according to some embodiments of this disclosure.

FIG. 2A schematically shows an exemplary static block 117 according to some embodiments of the disclosure. As shown, the exemplary static block 117 may be provided with one or more through holes 119 for amounting the static block 117 to the MLC interface plate 103 by long screws. The static block 117 has an inner surface 121. The inner surface 121 of the static block 117 and the plurality of beam shaping leaves 116 can be constructed and/or arranged such that if the inner surface 121 and the plurality of beam shaping leaves 116 were imaginarily extended in the direction toward the radiation source 104, they generally converge at an imaginary line across the source 104. In some variations, the static block 117 may include a step feature, and the through hole(s) may be provided in the step as will be described in greater detail below in conjunction with alternative embodiments.

Figure 3:
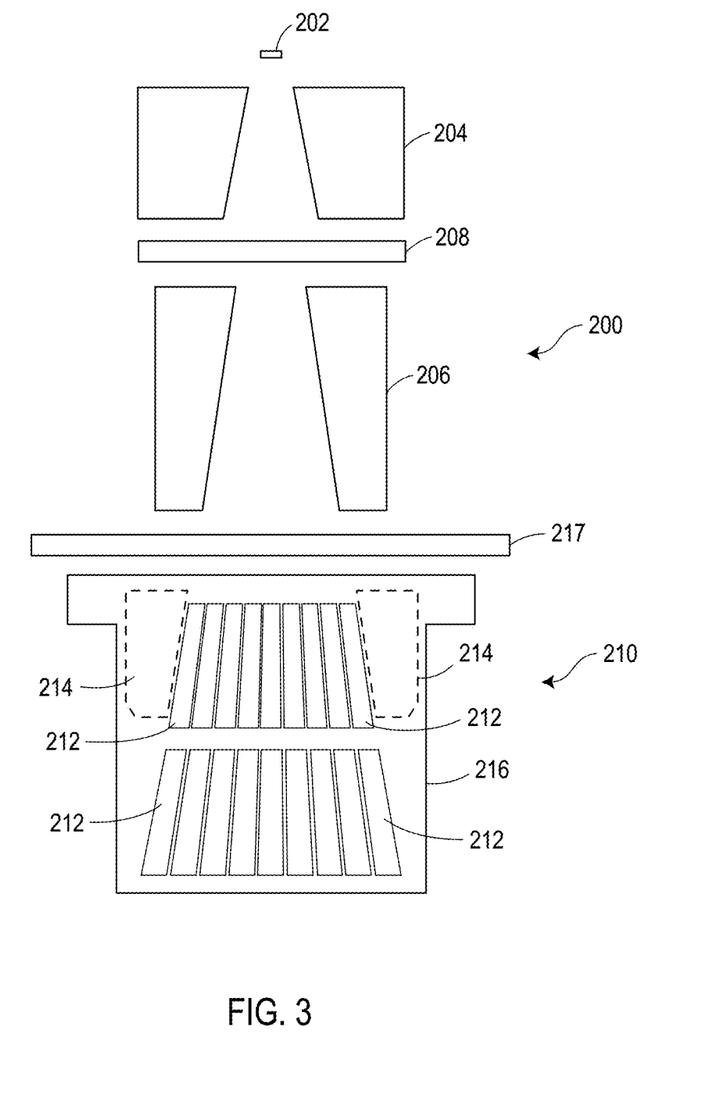
FIG. 3 is a side view of a radiation apparatus according to some alternative embodiments of this disclosure.
Figure 3A:
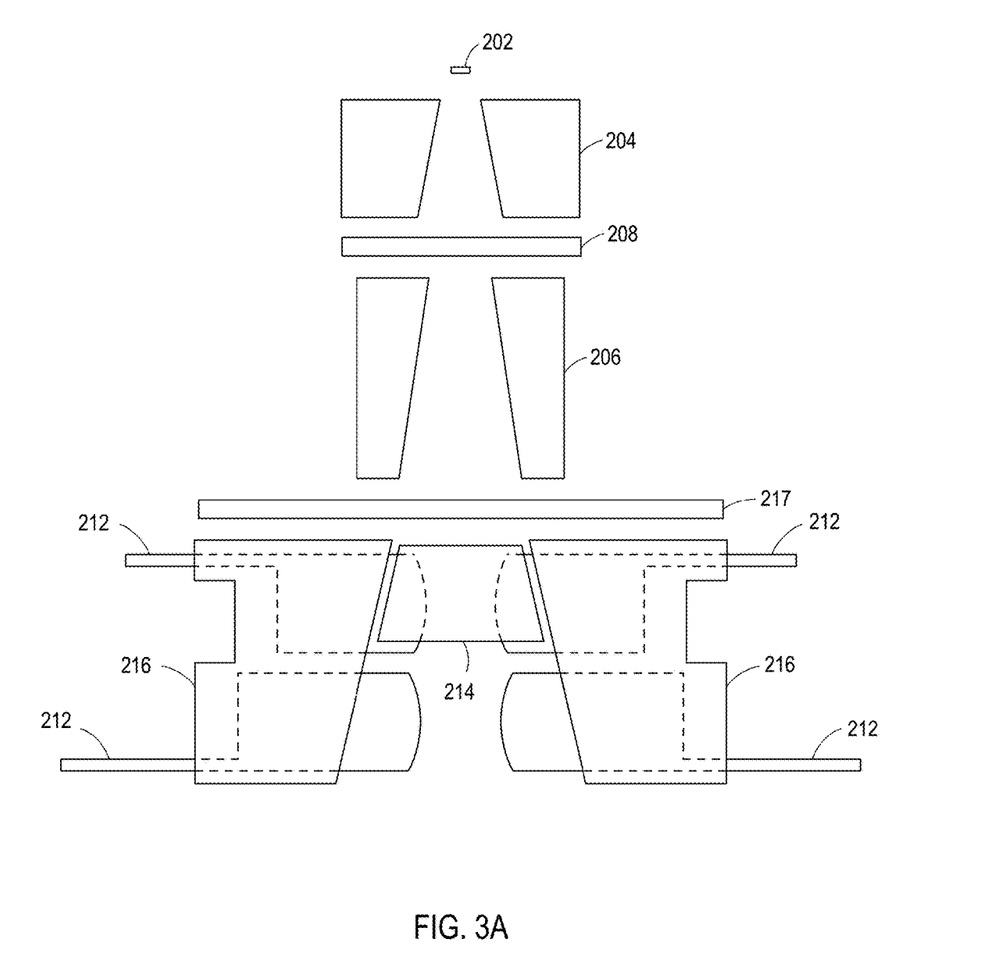
FIG. 3A is a front view of a radiation apparatus according to some alternative embodiments of this disclosure.

Referring now to FIGS. 3 and 3A-3D, an alternative embodiment of a radiation apparatus 200 according to embodiments of this disclosure will now be described. FIG. 3 is a side view of the radiation apparatus 200. FIG. 3A is a front view of the radiation apparatus 200. As shown, the radiation apparatus 200 includes a radiation source 202 that can produce radiation beams such as x-rays or other types of radiation. The radiation apparatus 200 may include a primary collimator 204, optionally a secondary collimator 206, which may have a circular or square aperture to generally limit the extent of the beam, and an ion chamber 208 to monitor the parameters of the beam. The radiation apparatus 200 may further include an MLC assembly 210 constructed or configured to further collimate the beam to provide a treatment field with a size and/or shape generally conforming to an intended target in the isocenter plane. The MLC assembly 210 of this disclosure can significantly reduce extra-focal radiation leakage as will be described in greater detail below.

In comparison with FIG. 2, the radiation apparatus 200 shown in FIGS. 3 and 3A does not require a flattening filter although a flattening filter can be optionally included. Further, the radiation apparatus 200 shown in FIGS. 3 and 3A does not require movable collimation X and Y jaws although one or more sets of movable collimation jaws may be included.

Referring to FIGS. 3 and 3A, the MLC assembly 210 may include a plurality of beam shaping leaves 212 and one or more static blocks 214. The plurality of beam block leaves 212 may be arranged in two or more different levels as shown. To simplify description and illustration, two levels of beam shaping leaves 212, a first level proximal to the radiation source 202 and a second level distal to the radiation source 202, are shown. It will be appreciated that the plurality of beam shaping leaves 212 can be arranged in more than two different levels. At each level, a plurality of beam shaping leaves 212 may be arranged in two opposing banks forming a plurality of pairs of leaves. Each leaf of a leaf pair in a bank can be longitudinally movable relative to the other leaf of the pair in the opposing bank. In some embodiments, the two or more levels of leaves 212 can be arranged in parallel such that the leaves 212 at different levels may longitudinally travel in a same direction. For example, the two or more levels of MLC leaves 212 may be arranged such that all the leaves 212 in the MLC assembly 210 can travel in e.g. the X-direction generally traverse to the beam direction when in use. U.S. Pat. No. 8,637,841 issued Apr. 24, 2015 entitled "Multi Level Multileaf Collimators" describes various embodiments of a multileaf collimator comprising beam shaping leaves arranged in two or more different levels. The disclosure of U.S. Pat. No. 8,637,841 is incorporated herein by reference in its entirety.

Figure 3B:
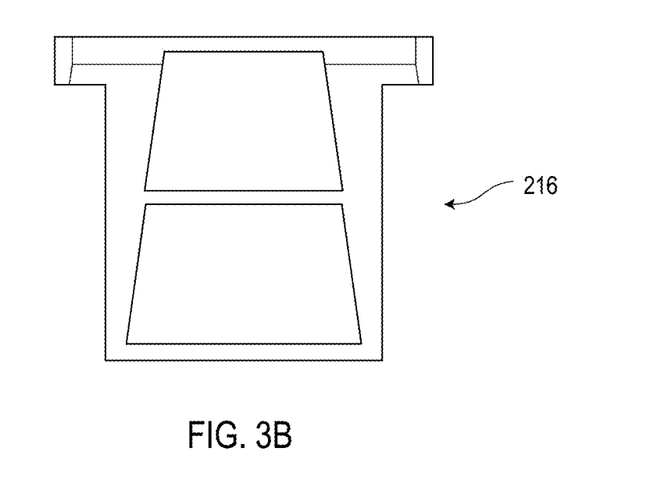
FIG. 3B is a front view of an MLC leaf box structure according to some embodiments of this disclosure.
Figure 3C:
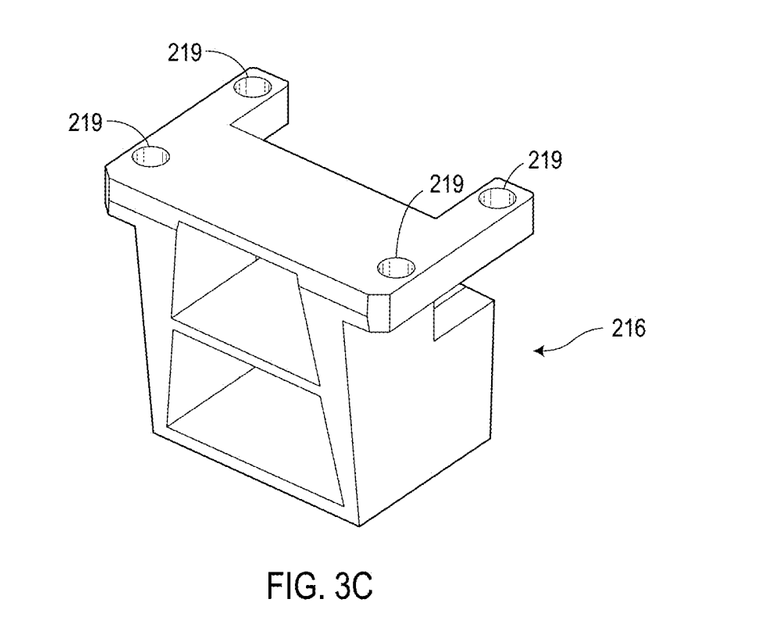
FIG. 3C is a perspective view of an MLC leaf box structure according to some embodiments of this disclosure.

The beam shaping leaves 212 may be contained or supported by one or more box structures 216, which in turn may be mounted to an MLC interface plate 217. FIGS. 3B and 3C depict an exemplary box structure 216 that can be used to contain or support one or two opposing banks of MLC leaves 212. As shown, the box structure 216 may be constructed such that a bank of beam shaping leaves 212 may be arranged in two levels. Features 219 may be provided for mounting the box structure 216 to the interface plate 217. Once the beam shaping leaves 212 are installed, the box structures 216 may be mounted to the interface plate 217, forming a two-level MLC with two opposing banks. Space between the two box structures 216 may be allocated for mounting static outboard blocks 214, one on each side of the opposing banks.

Returning to FIGS. 3 and 3A, the static blocks 214 may be located adjacent to the outmost MLC leaves to block the scatter leakage path adjacent to the outermost MLC leaves. The static blocks 214 may be located generally symmetrically with respect to the centerline of the MLC assembly 210 (FIG. 3A). As shown in FIG. 3A, the static blocks 214 may be located in the spaces between the two box structures 216, which may be fixedly mounted to the interface plate 217.

The static blocks 214 may be mounted to the box structures 216. Alternatively, the static blocks 214 may be mounted to the interface pate 217 using e.g. through holes in the static blocks and long screws. Optionally dowel pins and/or precision surfaces may be used to mount the static blocks more precisely.

In some embodiments, the one or more static blocks 214 may be located at the second level of the MLC leaves 212 distal to the radiation source 202. The one or more static blocks 214 may be mounted to the MLC box structures 216 via proper mounting features in the static blocks 214 and the box structures 216. Mounting the static blocks 214 adjacent to the distal banks of beam shaping leaves 212 may provide better radiation scatter shielding because the static blocks 214 may block both upstream scatter and the scatter generated by the proximal and distal beam shaping leaves 212 themselves.

In some embodiments, the one or more static blocks 214 may be located at the first level MLC leaves 212 proximal to the radiation source 202, as depicted in FIGS. 3 and 3A. The static blocks 214 may be provided with one or more through holes to allow them to be mounted to the interface plate 217 with long screws. Mounting the static blocks 214 adjacent to the proximal bank of the MLC beam shaping leaves allows for smaller and thus less expensive static blocks. The static blocks 214 can be located in the spaces between the leaf boxes (FIG. 3A), and, as such, modifications to the existing MLC boxes such as potentially another machining setup to add the mounting features for the static blocks would not be required. This design and mounting method can also simplify the manufacturing of the static blocks and reduce the cost of the parts. The design does not require precision tolerances for the mounting features or for the outside dimensions. This can further reduce the manufacturing cost without significantly sacrificing performance. The use of through holes and long screws increases the ability of the joint to resist loosening of the fasteners.

The design, construction, and leakage performance of the static blocks can be guided using Monte Carlo simulation. Conventionally, collimator leakage shielding design is developed based on a trial-and-error approach, which requires costly schedules, budgets and resources, and results in heavy and costly shielding parts and assembly. Collimator leakage performances are unknown until prototypes are constructed and actual measurements are made. In addition, traditional collimator design works to ensure that leakage measurements pass the IEC leakage requirements at distances larger than 0.5 m from isocenter, ignoring the leakage values in the area immediately outside the largest treatment field. As a result, leakage hot spots may exist outside the intended treatment area within distances less than 0.5 m from isocenter.

In general, Monte Carlo methods are statistical simulation methods. They are a numerical solution to a problem that models objects interacting with other objects or their environment based upon simple object-object or object-environment relationships. They represent an attempt to model a system through direct simulation of the essential physics interactions of the system in question. Various aspects of Monte Carlo methods are described in A. Bielajew, "Fundamentals of the Monte Carlo Method for Neutral and Charged Particle Transport," The University of Michigan, Ann Arbor, Mich., (2001) (hereafter the "Bielajew publication"). The disclosure of the Bielajew publication is incorporated herein by reference in its entirety. U.S. application Ser. No. 14/851,646 filed Sep. 11, 2015 entitled "Radiation Shields for LINAC Head and System" discloses various embodiments using Monte Carlo simulation in designing radiation head shields and system shields. The disclosure of U.S. application Ser. No. 14/851,646 is incorporated herein by reference in its entirety.

The materials suitable for constructing static blocks may include tungsten, lead or steel alloys, and other radiation attenuating materials known in the art. The thickness, size, and/or shape of the static blocks can be calculated using various algorithms or computer software. Parameters such as the angular distribution of radiation generated and propagating from a source, the angular function of thickness of a material in attenuating the radiation to a certain level of its original value, or other Monte Carlo simulation data or empirical data can be used as calculation inputs, which can then calculate the shield thickness needed for attenuating radiation to a specified value for a specified direction.

Figure 3D:
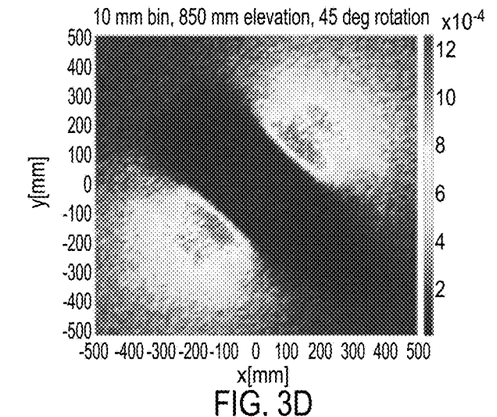
FIG. 3D is a Monte Carlo simulation image showing patient plane extra-focal leakage in the proximity of an intended treatment field when no outboard blocks are included in the radiation apparatus, 1×1 m2 plane is shown.
Figure 3E:
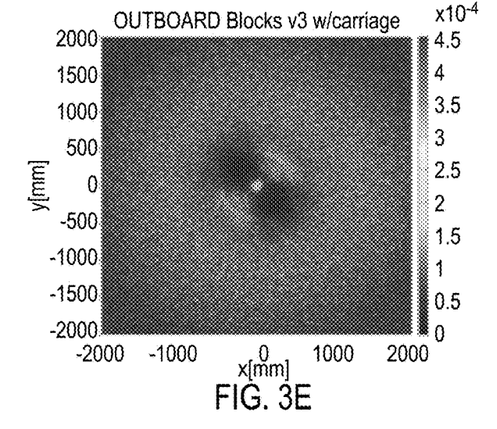
FIG. 3E is a Monte Carlo simulation image showing significant reduction of patient plane extra-focal leakage in the radiation apparatus depicted in FIGS. 3 and 3A which includes outboard blocks according to embodiments of this disclosure, 4×4 m2 plane is shown.

FIGS. 3D and 3E demonstrate the performance of the radiation apparatus of this disclosure in reducing extra-focal leakage as compared with conventional radiation apparatuses. FIG. 3D is a Monte Carlo simulation image showing radiation leakage in a conventional radiation apparatus that does not include static blocks. FIG. 3D shows that without static blocks, the extra-focal leakage in the radiation apparatus is significant. Hot spot appears outside the area covered by the MLC, and the leakage is as high as 0.1 percent. FIG. 3E is a Monte Carlo simulation image showing radiation leakage in the radiation apparatus depicted in FIGS. 3 and 3A that includes static blocks. FIG. 3E shows that with static blocks, the extra-focal leakage in the radiation apparatus of this disclosure is significantly reduced. The extra-focal leakage outside the area covered by the MLC is only about 0.01%.

Figure 3F:
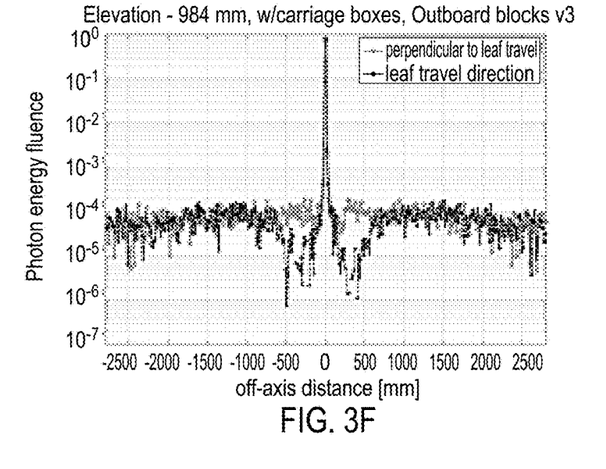
FIG. 3F shows the relative photon energy fluence versus off-axis distance in the patient plane according to some embodiments of the disclosure.

FIG. 3F shows the relative extra-focal dose versus off-axis distance in the patient plane, up to 2.5 m from isocenter, in the radiation apparatus shown in FIGS. 3 and 3A according to this disclosure. No extra-focal dose "humps" are observed in the radiation apparatus of this disclosure, independent of the field size, indicating that the static blocks efficiently stop the extra-focal scatter. The extra-focal leakage is remarkably as low as about 100 ppm or 0.01% of the dose delivered to iso-center. (i.e. targeted tumor location). This dramatically reduces the dose delivered to healthy tissues comparing to the prior art.

Figure 4A:
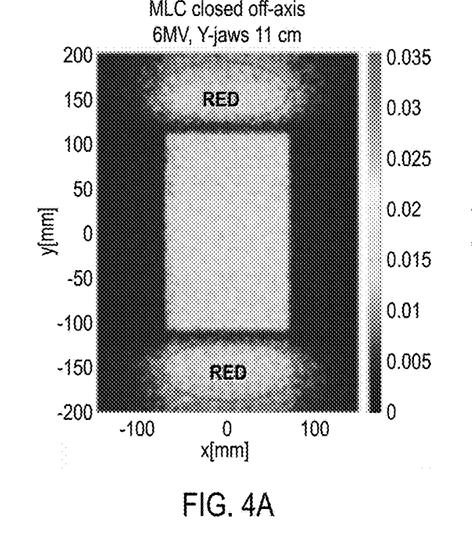
FIG. 4A is a Monte Carlo simulation image showing the out of field dose at 6 MV in a conventional radiation apparatus depicted in FIG. 1, with the MLC leaves being closed under one of the X-jaws.

FIG. 4A is a Monte Carlo simulation image showing the out of field dose for 6 MV photon beams on a conventional radiation apparatus shown in FIG. 1. In the illustrated example, the lower X-jaws are positioned at ±7 cm and the upper Y-jaws at ±11 cm respectively. The MLC leaves are closed off-axis (under one of the X-jaws). FIG. 4A shows that significant extra-focal leakage appears at y=±15 cm. The out-of-field dose (OOFD) is as large as 1.5% y=±15 cm for 6 MV photon beams. In FIG. 4A, the OOFD was normalized to the 10×10 cm$^2$ open field at $D_{max}$=1.5 cm.

Figure 4B:
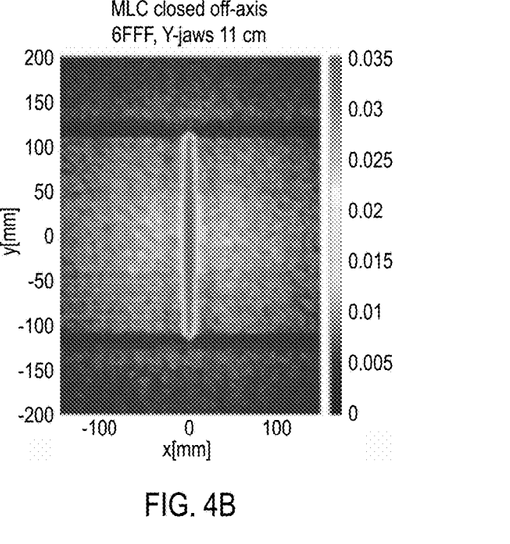
FIG. 4B is a Monte Carlo simulation image at 6FFF showing the out of field dose in a radiation apparatus free of a flattening filter or at 6FFF with the MLC leaves being closed on-axis.

FIG. 4B is a Monte Carlo simulation image showing the out of field dose for 6 MV photon beams on a radiation apparatus that is free of a flattening filter. In the illustrated example, the upper Y-jaws are positioned at ±11 cm. The MLC leaves are closed on-axis. FIG. 4B shows that the OOFD is approximately 0.7%.

Figure 4C:
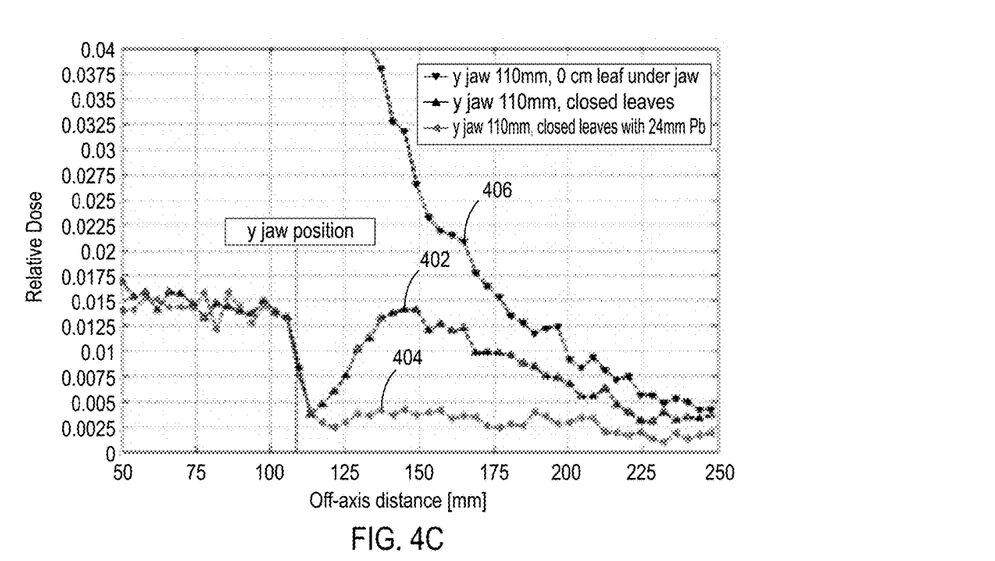
FIG. 4C shows the inline leakage profiles (i.e. perpendicular to leaf travel direction) according to some embodiments of the disclosure.

FIG. 4C shows the inline leakage profiles (profiles along the line perpendicular to the MLC leaf travel direction). Curve 402 is an inline profile for the field shown in FIG. 4A. An OOFD "hump" appears at about +15 cm on the inline profile 402. Curve 404 is an inline profile for a field (MLC closed) when two static blocks were equipped in the radiation machine shown in FIGS. 3 and 3A according to this disclosure. As shown in FIG. 4C, considerable leakage ~1.5%, comparable to the MLC transmission, is seen in the profile 402 when the Y-jaws are fully open. The OOFD can be lowered by limiting the field size in the Y-direction, as shown by the profile 404. The OOFD peak is not visible for largely open Y-fields as it is assimilated by the dose fall-off and penumbra regions of the profile, as seen in profile 406.

Figure 5:
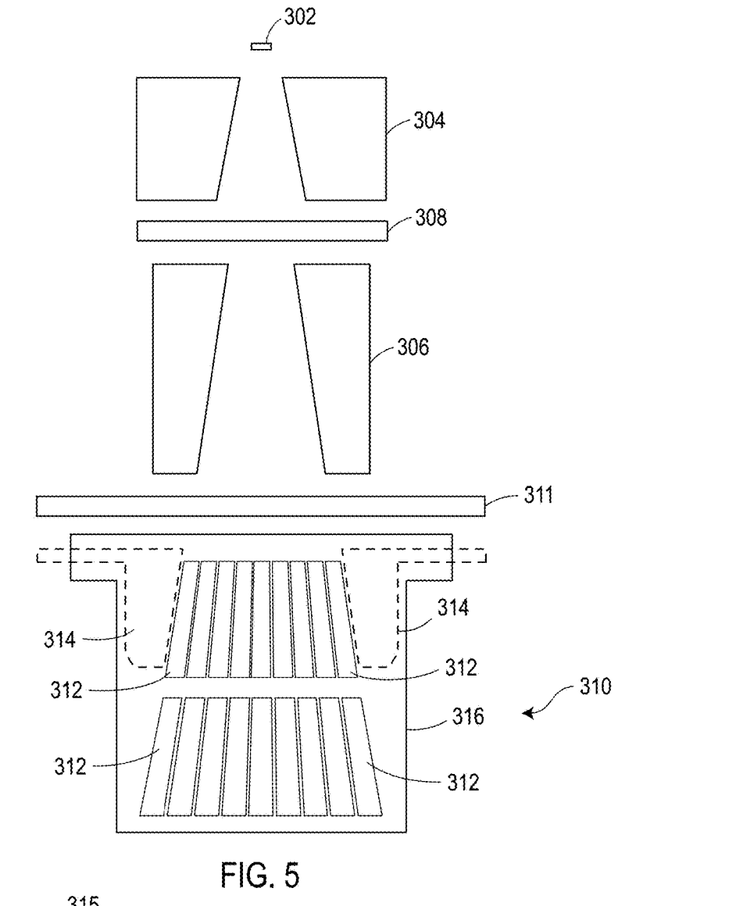
FIG. 5 is a side view of a radiation apparatus according to some alternative embodiments of the disclosure.
Figure 5A:
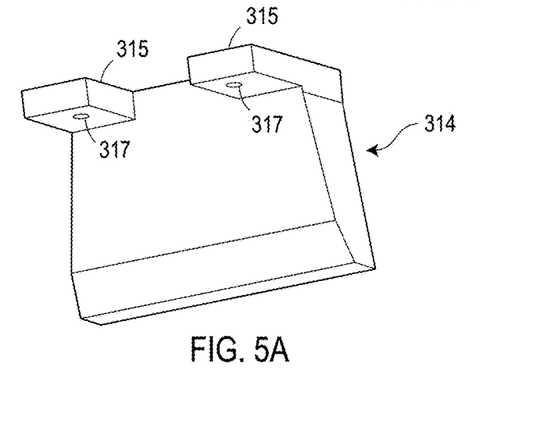
FIG. 5A is a perspective view of an exemplary outboard block according to some alternative embodiments of the disclosure.
Figure 5B:
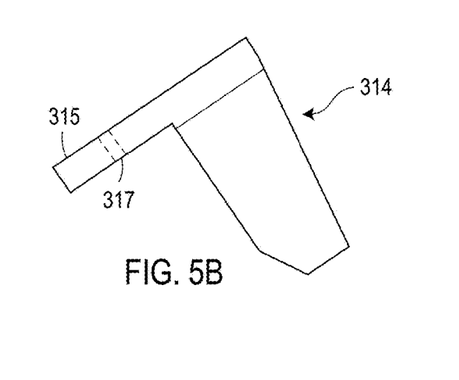
FIG. 5B is a side view of the exemplary outboard block shown in FIG. 5A.

FIGS. 5 and 5A-5B shows an alternative embodiment of a radiation apparatus 300 according to this disclosure. FIG. 5 is a side view of the radiation apparatus 300. FIG. 5A is a perspective view of an exemplary static block. FIG. 5B is a side view of the static block. The radiation apparatus 300 shown in FIG. 5 is similar to the radiation apparatus 200 shown in FIG. 3 in many aspects, and may include a radiation source 302, a primary collimator 304 and optionally a secondary collimator 306, an ion chamber 308, and an MLC assembly 310 supported by an interface plate 311. The MLC assembly 310 includes a plurality of beam shaping leaves 312, one or more static blocks 314, and one or more MLC box structure 316.

The static blocks 314 may include one or more step features 315 for mounting the static blocks to the interface plate 311. The outwardly extending steps 315 may be provided with one or more through holes 317 to allow mounting of the static blocks 314 by screws. This design may provide better extra-focal shielding as it moves the mounting through holes and screws from the shielding block main body.

A multileaf collimator assembly and a radiation apparatus comprising a multileaf collimator assembly have been described. The multileaf collimator assembly comprises one or two static blocks adjacent to the outermost MLC leaves. The multileaf collimator assembly can significantly reduce out-of-field dose, and as such, a superior radiation treatment quality can be ensured and the likelihood of secondary cancers and/or side effects is reduced. The extra-focal leakage reduction was from approximately 0.7% in the conventional radiation machine to less than 0.01%. In embodiments where the multileaf collimator assembly includes beam shaping leaves arranged in two or more levels, the design according to this disclosure can reduce the OOFD from approximately 0.1% to 0.01%.

The static blocks can be mounted directly on MLC interface plate between fixed MLC leaf boxes. No extra mounting surface would be required. The tolerances of the design allow the static blocks to be used "as sintered" with no additional machining necessary. The mounting provisions allow for quick assembling or disassembling, and easy access for the most likely service situations. The design of the static blocks and mounting procedure do not require motorization. Therefore, the costs associated with the material, space, assembly and service can be significantly reduced. A benchmarked Monte Carlo model was used to probe the leakage characteristics of the entire patient plane. This ensured the uniformity of the leakage map, absence of hot spots in the worst case configurations and results in very low average leakage. The design of the static blocks was driven by imposing as low as reasonably achievable extra-focal dose in the proximity of the intended treatment area.

Those skilled in the art will appreciate that various other modifications may be made within the spirit and scope of the invention. All these or other variations and modifications are contemplated by the inventors and within the scope of the invention.

What is claimed is:

1. A multileaf collimator assembly, comprising:
   a plurality of pairs of beam shaping leaves, leaves of each pair being movable relative to each other in a longitudinal direction, the plurality of pairs of beam shaping leaves comprising a first outermost pair of leaves and a second outermost pair of leaves opposite to the first outermost pair of leaves, leaves of each pair being driven by drive motors; and
   a first static block adjacent to the first outermost pair of leaves, the first static block being unmovable in the longitudinal direction relative to the plurality of pairs of beam shaping leaves and being constructed from a radiation attenuating material comprising tungsten or lead.

2. The multileaf collimator assembly of claim 1, further comprising a second static block adjacent to the second outermost pair of leaves, the second static block being unmovable in the longitudinal direction relative to the plurality of pairs of beam shaping leaves and being constructed from a radiation attenuating material comprising tungsten or lead.

3. A multileaf collimator assembly, comprising:
   a plurality of pairs of beam shaping leaves, leaves of each pair being movable relative to each other in a longitudinal direction, the plurality of pairs of beam shaping leaves comprising a first outermost pair of leaves and a second outermost pair of leaves opposite to the first outermost pair of leaves, leaves of each pair being driven by drive motors;
   a first static block adjacent to the first outermost pair of leaves and a second static block adjacent to the second outermost pair of leaves, the first and second static blocks being unmovable in the longitudinal direction relative to the plurality of pairs of beam shaping leaves and being constructed from a radiation attenuating material;
   further comprising one or more box structures supporting the plurality of pairs of beam shaping leaves, wherein the one or more box structure comprises:
   a first box structure supporting a first bank of the beam shaping leaves and a second box structure spaced apart from the first box structure supporting a second bank of the beam blocking leaves; and
   wherein the first and second static blocks are disposed in a space between the first and second box structures.

4. The multileaf collimator assembly of claim 3, wherein the first and second box structures are mounted to an interface plate.

5. The multileaf collimator assembly of claim 4, wherein the first and second static blocks are mounted to the interface plate.

6. The multileaf collimator assembly of claim 4, wherein at least one of the first and second static blocks is provided with one or more through holes to allow the at least one of the first and second static blocks to be mounted to the interface plate member by one or more screws.

7. The multileaf collimator assembly 6, wherein at least one of the first and second static blocks comprises one or more step features, and the one or more through holes are provided in the one or more step features.

8. The multileaf collimator assembly of claim 3, wherein the first and second static blocks are mounted to the first and second box structures.

9. The multileaf collimator assembly of claim 3, wherein the first and second box structures and the interface plate collectively are rotatable.

10. The multileaf collimator assembly of claim 2, wherein the plurality of pairs of beam shaping leaves are arranged at a first level proximal to a radiation source and a second level distal to the radiation source, and
    the first and second outermost pairs of beam shaping leaves and the first and second static blocks are located at the first level.

11. The multileaf collimator assembly of claim 2, wherein the plurality of pairs of beam shaping leaves are arranged at a first level proximal to a radiation source and a second level distal to the radiation source, and
    the first and second outermost pairs of beam shaping leaves and the first and second static blocks are located at the second level.

12. The multileaf collimator assembly of claim 2, wherein the multileaf collimator assembly has a center line across the longitudinal direction, and the first and second static blocks are disposed generally symmetrically on the center line of the multileaf collimator assembly.

13. The multileaf collimator assembly of claim 2, wherein the first and second static blocks have inner surfaces adjacent to the first and second outermost pairs of leaves, and the inner surfaces and the plurality of pairs of beam shaping leaves are arranged such that if imaginarily extended in a direction to a radiation source the inner surfaces and the plurality of pairs of beam shaping leaves generally converge at an imaginary line across the radiation source.

14. A radiation apparatus, comprising:
    a radiation source; and
    a multileaf collimator assembly, the multileaf collimator assembly comprising:
    a plurality of pairs of beam shaping leaves, leaves of each pair being movable relative to each other in a longitudinal direction, the plurality of pairs of beam shaping leaves comprising a first outermost pair of leaves and a second outermost pair of leaves opposite to the first outermost pair of leaves, leaves of each pair being driven by drive motors; and
a first static block adjacent to the first outermost pair of leaves; and
a second static block adjacent to the second outermost pair of leaves, wherein
the first and second static blocks are unmovable in the longitudinal direction relative to the plurality of pairs of beam shaping leaves and constructed from a radiation attenuating material comprising tungsten or lead.

15. The radiation apparatus of claim 14, wherein the radiation apparatus is free of a flattening filter.

16. The radiation apparatus of claim 14, wherein the radiation apparatus is free of motorized collimation jaws.

17. A radiation apparatus, comprising:
a radiation source; and
a multileaf collimator assembly, the multileaf collimator assembly comprising:
a plurality of pairs of beam shaping leaves, leaves of each pair being movable relative to each other in a longitudinal direction, the plurality of pairs of beam shaping leaves comprising a first outermost pair of leaves and a second outermost pair of leaves opposite to the first outermost pair of leaves, leaves of each pair being driven by drive motors; and
a first static block adjacent to the first outermost pair of leaves; and
a second static block adjacent to the second outermost pair of leaves,
wherein the first and second static blocks are unmovable in the longitudinal direction relative to the plurality of pairs of beam shaping leaves and constructed from a radiation attenuating material, and
wherein the multileaf collimator assembly comprises one or more leaf box structures supporting the plurality of pairs of beam shaping leaves, wherein the one or more leaf box structure comprises:
a first box structure supporting a first bank of the beam shaping leaves and a second box structure spaced apart from the first box structure supporting a second bank of the beam blocking leaves; and
wherein the first and second static blocks are disposed in a space between the first and second box structures.

18. The radiation apparatus of claim 17, wherein the first and second box structures are mounted to an interface plate.

19. The radiation apparatus of claim 18, wherein the first and second static blocks are mounted to the interface plate.

20. The radiation apparatus of claim 19, wherein at least one of the first and second static blocks is provided with one or more through holes to allow the at least one of the first and second static blocks to be mounted to the interface plate member by one or more screws.

21. The multileaf collimator assembly 20, wherein at least one of the first and second static blocks comprises one or more step features, and the one or more through holes are provided in the one or more step features.

22. The radiation apparatus of claim 17, wherein the first and second static blocks are mounted to the first and second box structures.

23. The multileaf collimator assembly of claim 15, wherein the multileaf collimator assembly has a center line across the longitudinal direction, and the first and second static blocks are disposed generally symmetrically on the center line of the multileaf collimator assembly.

24. The multileaf collimator assembly of claim 15, wherein the first and second static blocks have inner surfaces adjacent to the first and second outermost pairs of leaves, and the inner surfaces and the plurality of pairs of beam shaping leaves are arranged such that if imaginarily extended in a direction to a radiation source the inner surfaces and the plurality of pairs of beam shaping leaves generally converge at an imaginary line across the radiation source.

25. The radiation apparatus of claim 14, wherein
the plurality of pairs of beam shaping leaves of the multileaf collimator assembly are arranged at a first level proximal to the radiation source and a second level distal to the radiation source, and
the first and second outermost pairs of beam shaping leaves and the first and second static blocks are located at the first level.

26. The radiation apparatus of claim 14, wherein
the plurality of pairs of beam shaping leaves of the multileaf collimator assembly are arranged at a first level proximal to the radiation source and a second level distal to the radiation source, and
the first and second outermost pairs of beam shaping leaves and the first and second static blocks are located at the second level.

27. The multileaf collimator assembly of claim 3, wherein the first and second box structures each comprises an end surface having an aperture allowing the beam shaping leaves of the first and second banks to extend into or retract from the space between the first and second box structures, and wherein the end surfaces of the first and second box structures, if extended in a direction to a radiation source, converge at a line across the radiation source.

28. The multileaf collimator assembly of claim 3, wherein the first and second static blocks are constructed from tungsten, lead, or steel alloys.

29. The radiation apparatus of claim 17, wherein the first and second box structures each comprises an end surface having an aperture allowing the beam shaping leaves of the first and second banks to extend into or retract from the space between the first and second box structures, and wherein the end surfaces of the first and second box structures, if extended in a direction to the radiation source, converge at a line across the radiation source.

30. The radiation apparatus of claim 17, wherein the first and second static blocks are constructed from tungsten, lead, or steel alloys.

* * * * *